US006827216B2

(12) United States Patent
Foelster et al.

(10) Patent No.: US 6,827,216 B2
(45) Date of Patent: Dec. 7, 2004

(54) FIRST-AID DEVICE FOR MOTOR VEHICLES

(75) Inventors: Thomas Foelster, Grafenau (DE); Thomas Heckmann, Aidlingen (DE)

(73) Assignee: DaimlerChrysler AG, Stuttgart (DE)

( * ) Notice: Subject to any disclaimer, the term of this patent is extended or adjusted under 35 U.S.C. 154(b) by 23 days.

(21) Appl. No.: 10/153,885

(22) Filed: May 24, 2002

(65) Prior Publication Data

US 2002/0189968 A1 Dec. 19, 2002

(30) Foreign Application Priority Data

May 25, 2001 (DE) .......................................... 101 25 423

(51) Int. Cl.[7] .............................................. B65D 69/000
(52) U.S. Cl. ........................ 206/570; 206/225; 206/803; 383/38
(58) Field of Search ........................ 206/6.1, 225, 226, 206/373, 376, 570, 581, 747, 748, 749, 803; 383/38, 40

(56) References Cited

U.S. PATENT DOCUMENTS

| | | | |
|---|---|---|---|
| 657,463 A | * | 9/1900 | Simpson |
| 2,502,033 A | * | 3/1950 | Bohn .......................... 206/293 |
| 3,134,416 A | * | 5/1964 | Magyar |
| 3,221,959 A | * | 12/1965 | Southwick |
| 4,967,986 A | * | 11/1990 | Schildkraut |
| 5,002,401 A | * | 3/1991 | Blackman |
| 6,065,659 A | * | 5/2000 | Faz |
| 6,513,692 B1 | * | 2/2003 | Forgosh et al. |

FOREIGN PATENT DOCUMENTS

| | | |
|---|---|---|
| DE | 38 21 697 | 8/1990 |
| DE | 9316351.7 | 8/1994 |

OTHER PUBLICATIONS

German Office Action with English translation.

\* cited by examiner

*Primary Examiner*—David T. Fidei
(74) *Attorney, Agent, or Firm*—Crowell & Moring LLP

(57) ABSTRACT

A first-aid device for motor vehicles which has an elastic unrollable mat which is used as a carrier for items of first-aid equipment and has an essentially rectangular shape. In order to use existing storage space effectively and, in particular, to obtain a compact structural shape, the mat has a fastener on two longitudinal edges, so that it can be folded-up to form a flexible container. In the process, the fastener connects the longitudinal edges of the mat to form a stable, cylindrical container.

19 Claims, 4 Drawing Sheets

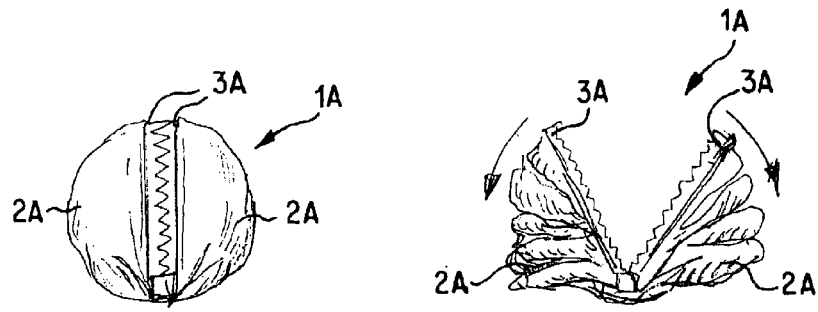
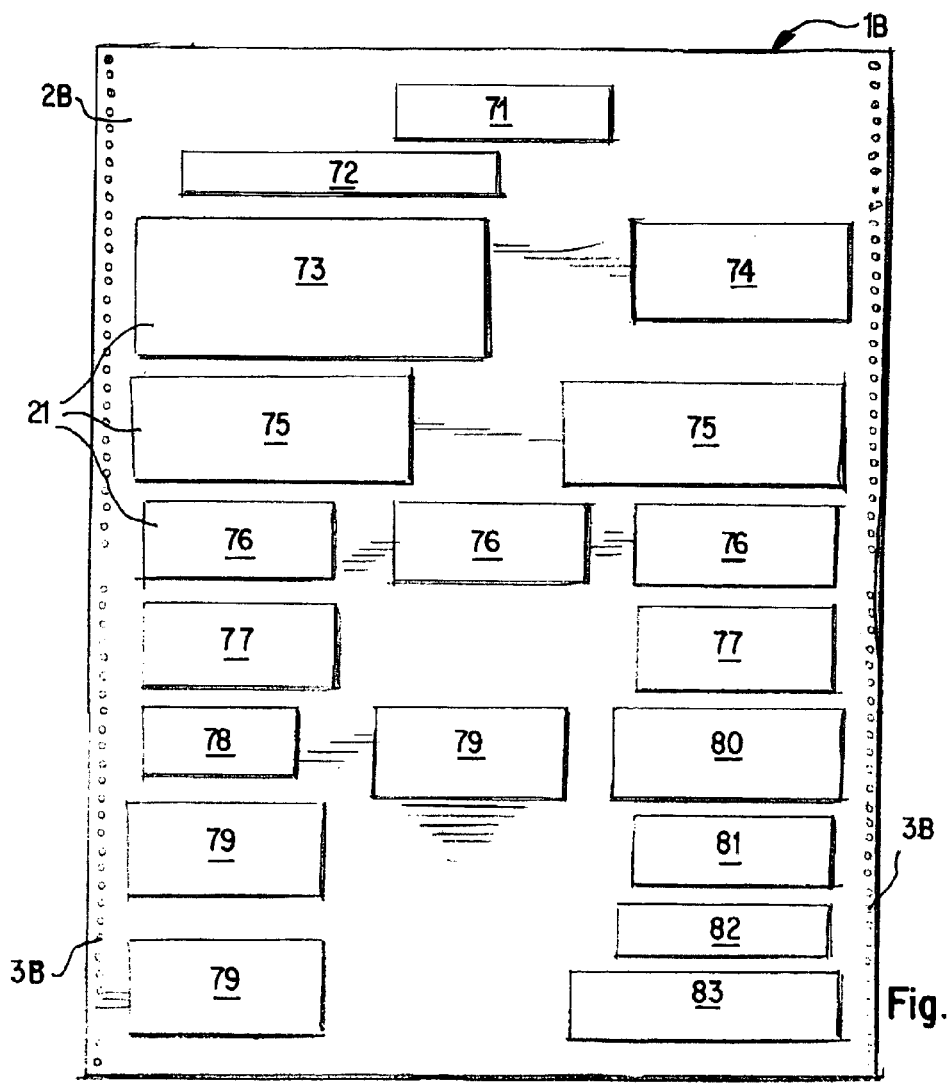

FIRST-AID DEVICE FOR MOTOR VEHICLES

BACKGROUND OF THE INVENTION

This application claims the priority of German Application No. 101 25 423.7, filed May 25, 2001.

The invention relates to a first-aid device for motor vehicles for holding first-aid equipment.

A first-aid box should be carried in every motor vehicle. Conventional first-aid boxes generally have a cuboidal and relatively rigid housing made of sheet metal or plastic. A first-aid box of this type is usually stored at a suitable point in the motor vehicle and is therefore generally fixed in the boot or trunk by means of straps. In the case of modern vehicles, the aim is for a construction which is as compact and as space-saving as possible. The space available for storage spaces is therefore becoming ever smaller. In addition, the storage spaces provided in the vehicle are often asymmetrical and/or relatively fissured. A conventional first-aid box with its rigid cuboidal housing cannot fully use a storage space of this type.

German Patent Document DE 38 21 697 A1 discloses a first-aid box which has an elastic mat which serves as a carrier for items of first-aid equipment. The mat has a plurality of depressions into which individual items can be placed loosely. For storage purposes, the mat is coiled up spirally. The spirally coiled-up mat is then secured against uncoiling by the free edge of the mat being secured, for example by a latching fastener. However, the mat is relatively thick and has little mechanical stability, and so the spirally coiled-up first-aid box is of quite large size and is not very comfortable to handle.

An object of the present invention is to provide a first-aid device which is suitable for holding first-aid equipment and is firstly of compact construction and secondly is easy to handle. The intention in particular is for the first-aid device to be storable in a simple and space-saving manner in fissured, preferably cylindrical spaces.

This object is achieved according to certain preferred embodiments of the invention by a first-aid device for motor vehicles, for holding first-aid equipment, having an elastic and unrollable mat which has an essentially rectangular shape and is designed as a carrier for items of first-aid equipment, wherein two parallel edges of the mat have each one part of a fastener and the mat can be folded-up in such a manner that the fastener connects the parallel edges to each other and the mat forms a cylindrical container.

In certain preferred embodiments of the invention, the mat has a fastener on two mutually parallel longitudinal sides. In this case, one part of the fastener is arranged on each of the edges. The two parts of the fastener are connected to each other in a frictional manner for closure purposes. For storage purposes, the mat is folded-up to form a cylindrical body, with the result that the parallel edges come into contact with, or overlap, the fastener. The two parts of the fastener are then situated directly next to each other and can be connected to each other. The mat, which is folded-up and is connected on its longitudinal sides to the fastener, forms a cylindrical container which holds first-aid equipment in its interior.

The container is easy to handle and has good stability if the fastener is designed as a linear fastener which connects the parallel edges over their entire length to each other according to certain preferred embodiments of the invention.

As a result, the flexible mat is stabilized mechanically and is easy to close. Provision is made according to certain preferred embodiments of the invention to design the fastener as a zip fastener or touch-and-close fastener, which permits particularly simple handling, since the mat can then be folded-up and closed in practically no time.

The mat can be formed with relatively thin walls from leather or imitation leather or from a plastic according to certain preferred embodiments of the invention. The mat is therefore hard-wearing and at the same time flexible. This is advantageous, since the mat forms the container wall and the flexible and hard-wearing wall can be adapted in a simple manner to fissured and/or undercut storage spaces. Also, the flexible container wall provides a good grip and therefore comfortable handling.

In certain embodiments of the invention, provision is made for the inside of the mat to have securing means and/or holders, preferably insertion pockets for items of first-aid equipment. These insertion pockets are matched in their shape to individual items of first-aid equipment and hold the said items in a form-fitting manner. The items therefore remain securely in their place even when the mat is open and even if the mat should be inadvertently knocked or overturned. It is advantageous according to certain preferred embodiments of the invention that the items of first-aid equipment are fixed securely on the mat, particularly if the open mat has to be transported.

The insertion pockets are advantageously arranged in such a manner that the folded-up mat or the container has a minimal volume according to certain preferred embodiments of the invention. Essentially cuboidal insertion pockets are arranged in particular with their longer extent in the direction of the longitudinal axis of the cylindrical container according to certain preferred embodiments of the invention. The items situated in the pockets can thus additionally stabilize the container mechanically.

In order to obtain a small volume of the container over a long period, it is desirable to be assured that after use, the first-aid equipment can again be packed precisely into the insertion pockets in such a manner that the small structural volume is obtained. To this end, provision is made for the mat to advantageously have an order system according to certain preferred embodiments of the invention. The insertion pockets preferably have an unambiguous shape which is matched to the shape of the individual items of first-aid equipment in such a manner that only one particular item of the first-aid equipment can be inserted into each insertion pocket. In order to enable rapid and convenient packing, the insertion pockets may also have a marking or label which makes it easier to find the correct insertion pocket.

Other objects, advantages and novel features of the present invention will become apparent from the following detailed description of the invention when considered in conjunction with the accompanying drawings.

BRIEF DESCRIPTION OF THE DRAWINGS

FIG. 3B is a view similar to FIG. 3, but showing a further embodiment of the invention wherein the connecting seam extends over the top and to the bottom of the container;

FIG. 3C is a view of the FIG. 3B arrangement shown in a partly open position;

FIG. 4 is a schematic view of a further embodiment of first-aid container according to the invention, shown in a flat unfolded open position;

DETAILED DESCRIPTION OF THE DRAWINGS

Figure 1:
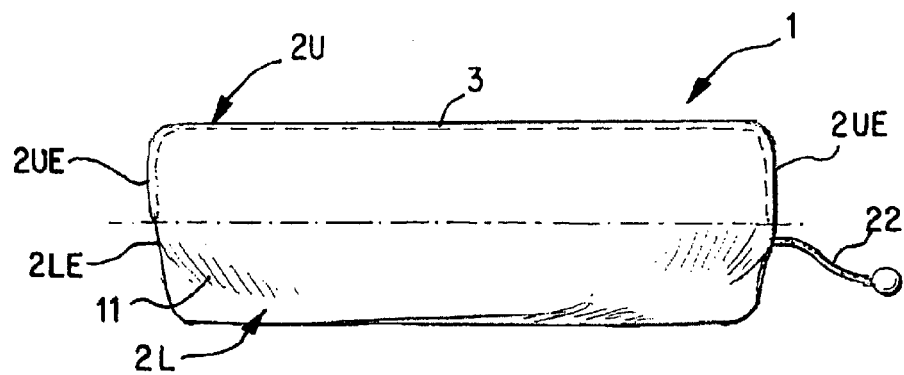
FIG. 1 is a side view of a first-aid device which is folded-up and closed to form a container constructed according to a first preferred embodiment of the invention.
Figure 2:
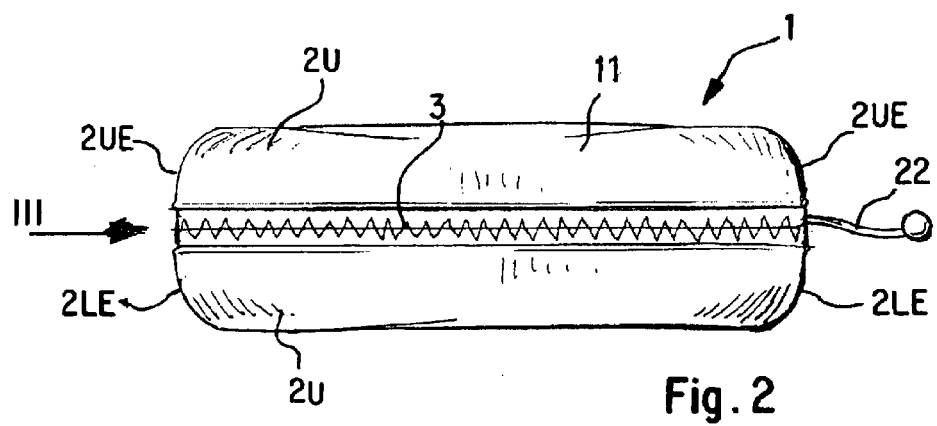
FIG. 2 is a plan view of a first-aid container of FIG. 1 shown in a closed condition.

FIG. 1 shows a side view of a first embodiment of a first-aid device according to the invention, with the first-aid container 1 in a closed condition The container 1 has a cylindrical construction and a bevelled contour on the end sides as illustrated. The first-aid container 1 is designed in a complementary manner with respect to a storage space present in the motor vehicle and is packed into the latter in a precisely fitting manner when not in use. In order to be able to remove the first-aid container 1 in a simple and convenient manner from a storage space of this type, the first-aid container 1 has a cord 22 on its end side. The cord 22 is connected fixedly to the first-aid container. In order to remove the first-aid container from a storage space, the cord 22 is pulled. The first-aid container can thus be removed simply and rapidly from a storage space even in constricted spatial conditions.

The lower half of the first-aid container of FIGS. 1–4 is formed as a half cylindrical shell 2L and the upper half is formed of quarter cylindrical shaped sections 2U. The end sections 2LE in the lower part 2L are formed with a beveled contour on the end sides as illustrated. In a similar manner, the upper end sections 2UE is also formed with a beveled contour as illustrated.

Figure 3:
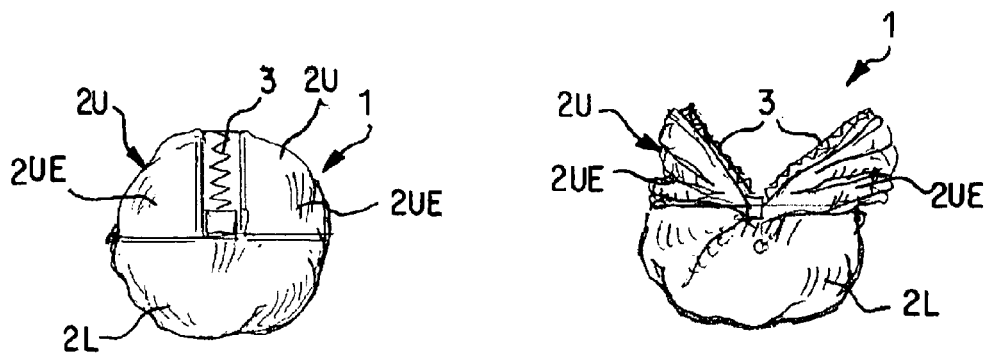
FIG. 3 is an end view of the container of FIG. 2 taken in the direction of arrow III in FIG. 2.

The first-aid container 1 has a fastener 3 on its upper side. This fastener 3, can be seen in the top view of FIG. 2 and the end views of FIG. 3 and 3A and includes a fastener 3 extending over its upper side. This fastener 3 extends along the upper horizontal edge of the first-aid container 1. The walls 11 of the first-aid container is formed by a flexible mat section 2U, 2L as shown in FIG. 3, the mat sections 2U are folded-up from the upper half of the cylindrical container when in a closed position. One part of the fastener 3 is providing on each of the mutually free edges of the upper mat sections 2U. The fastener 3 connects the edges of the mat to each other, with the folded-up mat 2 forming a closed body with a substantially round cross section, as illustrated in FIG. 3. The first-aid equipment is held in the interior of this body.

The mat 2, 2U, 2L is formed from a flexible and hard-wearing fabric, such as, for example, plyethylene or polyamide, or from a plastic blended fabric. As a result, the mat has relatively low height, which has a positive effect on the utilization of space. This mat secures items of first-aid equipment on its inside. The mat can also be advantageously be imprinted and/or provided with a label on its outside which forms the outer wall of the container.

Figure 3A:
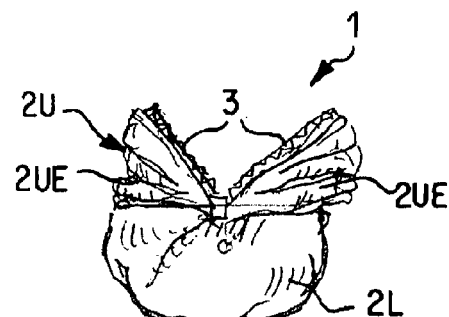
FIG. 3A is a view similar to FIG. 3, but showing the container in an open position.

If the fastener 3 is opened, the mat sections 2U can be opened out, as illustrated in FIG. 3A so as to provide access to the interior of the container 1. The fastener 3 can be formed as a zipper, a velcro fastener or the like.

FIGS. 3B and 3C depict an alternative arrangement of a container 1A which differs from container 1 of FIGS. 1–3A in that the fastener 3A extends along the horizontal upper edge, as well as to the bottoms of the end sections 2A, which are formed as two half cylindrical sections which can be folded down flat when in an open position. When folded flat, the arrangement of FIGS. 3B and 3C exhibits an essentially rectangular shape presenting the individual items of first-aid equipment in a clear manner arranged next to one another, analogous to the arrangement illustrated in FIG. 4 and described below.

Figure 5:
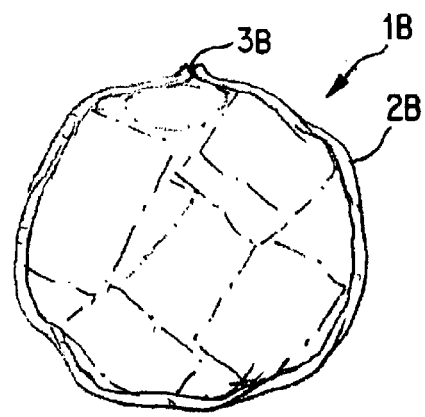
FIG. 5 is an end view of a container made from the unfolded mat of FIG. 4, shown in a closed position.
Figure 6:
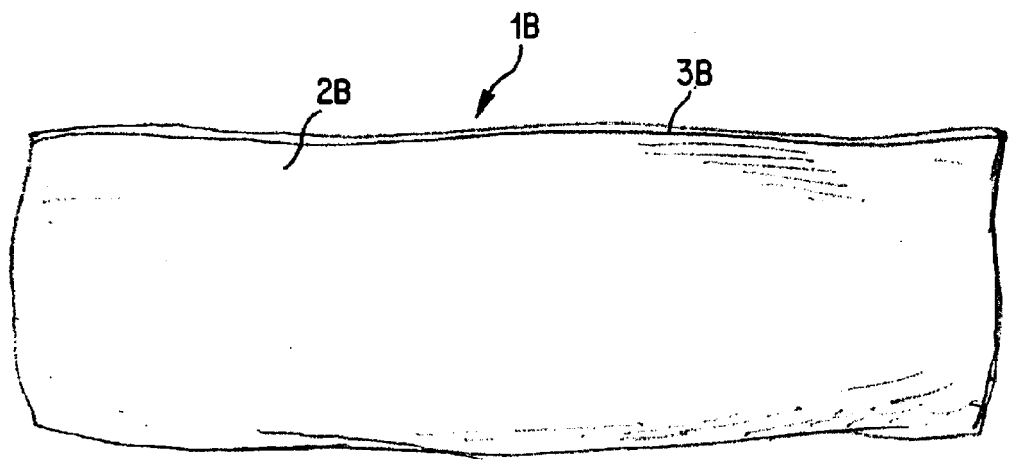
FIG. 6 is a side view of the container of FIGS. 4 and 5, shown in a closed position.

FIGS. 4–6 illustrate another embodiment of a first-aid container 1B which in the open condition shown in FIG. 4 has an essentially a rectangular flat shape. On the inside of the mat 2B a plurality of securing means and holders 21, schematically depicted at reference characters 71–83, such as insertion compartments, storage compartments, or retaining loops or the like are provided for securing and storing individual items of first-aid equipment, such as first-aid packets, plasters, scissors, rescue blanket, etc. Preferably, such items of first-aid equipment are provided for holding on the mat 2B in an appropriate number which is prescribed by standard. In this arrangement, the items are inserted into the securing means and/or holders 21 and are fixed by the latter on the mat 2B. The mat 2B can therefore also be transported when opened out without individual items of first-aid equipment becoming jumbled or being lost. Moreover, when the mat 2B is opened out, the items of first-aid equipment are presented in a clear manner, so that the items can be found rapidly and rapid assistance is possible.

In the arrangement of FIGS. 4–6, the arrangement of the securing means and holders is selected in such a manner that mat 2B can be folded-up along a longitudinal axis. The securing means and holders are, in particular, arranged and offset with respect to one another in such a manner that the folded-up mat 2B has a minimal volume. The base surface of the securing means and holders is essentially rectangular, the longer extent of the base surface being aligned parallel to the longitudinal axis. In the FIG. 4 showing of an exemplary arrangement of the securing means in holders 21, the same are arranged with consideration of the dimensions of the items of first-aid equipment, offset with respect to one another in such a manner that when the mat is folded-up, the first-aid container 1B has a small volume. In order to optimally use this space available when the mat is folded-up to form a cylindrical shape (compare FIGS. 5 and 6), one flat item, and one tall item are arranged diagonally opposite each other in each case on the inside of the cylindrical container. In order to further reduce the volume of the container, use can be made of first-aid packets which have a lower height than standard first-aid packets.

In order for it to be possible to close the first-aid container 1B comfortably, even with repeated packing and unpacking, and in particular in order to have a volume which is small over a long period, the items of a first-aid equipment have to be packed correctly. In order to bring this about, and in particular, to make rapid and convenient packing possible, the mat 2B has an order system which is designed as follows. The securing means and holders have an unambiguous shape, identified schematically at reference characters 71–83, which is matched to the shape of the respective particular item of the first-aid equipment which is to be fixed in the securing means and/or holders 21. In order to make it easier to pack the items, the mat 2B and/or the securing means or holders 21 having markings and/or labels which describe the item to be packed, or an image thereof is shown. Provision is also made in particular to provide the individual items of first-aid equipment and the securing means and/or holders 21 with unambiguous colored markings in each case which enable simple and efficient packing. In the embodiment of FIGS. 4–6, the fastener structures 3B are disposed along respective opposite longitudinal edges of the mat 2B, and when the container is closed, these fasteners 3B are connected together along a horizontal seam at the top of the container 1B as shown in FIGS. 5 and 6. In this embodiment, the ends of the container 1B are open, with the first-aid equipment items being shown schematically in-lines in FIG. 5.

Figure 7:
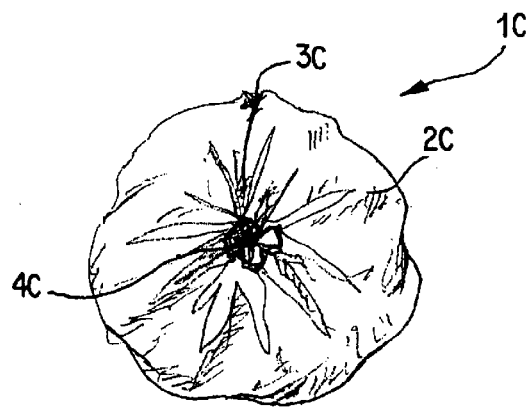
FIG. 7 is an end view of a further embodiment of a first-aid container similar to FIG. 4, but also including closeable ends.
Figure 8:
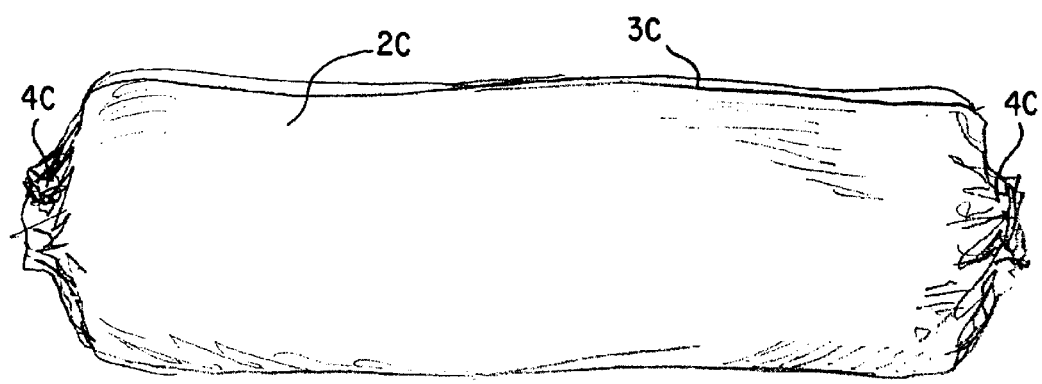
FIG. 8 is a side view of a closed first-aid container according to the arrangement of the embodiment of FIG. 7.

FIGS. 7 and 8 schematically depict a further embodiment of a first-aid container 1C, which is similar to the container of FIGS. 4–6, except that the ends have sufficient additional flexible mat material for the mat 2C so that they can be closed, for example by tie mechanisms 4C. This embodiment of FIGS. 7 and 8 can also be folded out in a substantially rectangular planar form as shown in FIG. 4.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. First-aid device for motor vehicles, for holding first-aid equipment, comprising an elastic mat which has an essentially rectangular shape and is designed as a carrier for items of first-aid equipment, wherein two parallel edges of the mat each have one part of a fastener, wherein the mat can be folded-up in such a manner that the fastener connects the parallel edges to each other and the mat forms a cylindrical container, wherein the fastener is designed as a linear fastener which extends over the entire length of the parallel edges and which can connect the parallel edges over their entire length to each other, and wherein the inside of the mat has securing means for securing items of first-aid equipment.

2. First-aid device for motor vehicles, for holding first-aid equipment, Comprising an elastic mat which has an essentially rectangular shape and is designed as a carrier for items of first-aid equipment, wherein two parallel edges of the mat each have one part of a fastener, wherein the mat can be folded-up in such a manner that the fastener connects the parallel edges to each other and the mat forms a cylindrical container, wherein the fastener is designed as a linear zip or touch-and-close fastener which extends over the entire length of the parallel edges and which can connect the parallel edges over their entire length to each other, and wherein the inside of the mat has securing means for securing items of first-aid equipment.

3. First-aid device according to claim 1, wherein the securing means have essentially rectangular base surfaces.

4. First-aid device according to claim 2, wherein the securing means have essentially rectangular base surfaces.

5. First-aid device according to claim 1, wherein the securing means are arranged in such a manner that the cylindrical container has a minimal volume.

6. First-aid device according to claim 2, wherein the securing means are arranged in such a manner that the cylindrical container has a minimal volume.

7. First-aid device according to claim 1, wherein the securing means are arranged in such a manner that the securing means, when filled with first-aid equipment, stabilize the cylindrical shape of the container.

8. First-aid device according to claim 3, wherein the securing means are arranged in such a manner that the securing means, when filled with first-aid equipment, stabilize the cylindrical shape of the container.

9. First-aid device according to claim 5, wherein the securing means are arranged in such a manner that the securing means, when filled with first-aid equipment, stabilize the cylindrical shape of the container.

10. First-aid device according to claim 1, wherein the mat has an order system which is designed for simple and space-saving parking by the securing means having an unambiguous shape which is matched to the dimensions of the items of first-aid equipment.

11. First-aid device according to claim 1, wherein the securing means are designed as insertion pockets.

12. First-aid device for motor vehicles, for holding first-aid equipment, comprising an elastic mat which has an essentially rectangular shape and is designed as a carrier for items of first-aid equipment, wherein two parallel edges of the mat each have one part of a fastener, wherein the mat can be folded-up in such a manner that the fastener connects the parallel edges to each other and the mat forms a cylindrical container, wherein the fastener is designed as a linear fastener which extends over the entire length of the parallel edges and which can connect the parallel edges over their entire length to each other, and wherein said mat is configured to have a semi-cylindrical shape closed at the longitudinal ends, with upper quarter cylindrical sections which contain the parallel edges with the fastener parts.

13. First-aid device for motor vehicles, for holding first-aid equipment, comprising an elastic mat which has an essentially rectangular shape and is designed as a carrier for items of first-aid equipment, wherein two parallel edges of the mat each have one part of a fastener, wherein the mat can be folded-up in such a manner that the fastener connects the parallel edges to each other and the mat forms a cylindrical container, wherein the fastener is designed as a linear fastener which extends over the entire length of the parallel edges and which can connect the parallel edges over their entire length to each other, and wherein the mat, when in the folded-up closed position, exhibits two facing semi-cylindrical shapes connected together by the fastener parts.

14. First-aid device for motor vehicles, for holding first-aid equipment, comprising an elastic mat which has an essentially rectangular shape and is designed as a carrier for items of first-aid equipment, wherein two parallel edges of the mat each have one part of a fastener, wherein the mat can be folded-up in such a manner that the fastener connects the parallel edges to each other and the mat forms a cylindrical container, wherein the fastener is designed as a linear fastener which extends over the entire length of the parallel edges and which can connect the parallel edges over their entire length to each other, and wherein the inside of the mat has holders adapted to hold items of first-aid equipment.

15. First-aid device according to claim 14, wherein the holders have essentially rectangular base surfaces.

16. First-aid device according to claim 14, wherein the holders are arranged in such a manner that the cylindrical container has a minimal volume.

17. First-aid device according to claim 14, wherein the holders are arranged in such a manner that the holders, when filled with first-aid equipment, stabilize the cylindrical shape of the container.

18. First-aid device according to claim 14, wherein the mat has an order system which is designed for simple and space-saving parking by the holders having an unambiguous shape which is matched to the dimensions of the items of first-aid equipment.

19. First-aid device according to claim 14, wherein the holders are designed as insertion pockets.

* * * * *